United States Patent [19]

Dowdell et al.

[11] Patent Number: 4,925,285

[45] Date of Patent: May 15, 1990

[54] APPARATUS TO PERMIT ANATOMICAL SELF EXAMINATION

[76] Inventors: James F. Dowdell, 2523 - 106 St., Edmonton, Alberta, Canada, T6J 4K2; Eleanora G. Wilson, 11626 - 92 Street, Edmonton, Alberta, Canada, T5G 0Z9

[21] Appl. No.: 357,346

[22] Filed: May 26, 1989

[51] Int. Cl.[5] .................... A61B 1/00

[52] U.S. Cl. .................... 350/621; 350/616; 312/324; 312/227

[58] Field of Search .................... 248/466, 469, 472, 474; 211/13, 169; 312/224, 225, 226, 227, 324, 244; 160/135, 351, 352; 52/34; 350/612, 615, 616, 631, 632, 621

[56] References Cited

U.S. PATENT DOCUMENTS

| | | | |
|---|---|---|---|
| 260,707 | 5/1926 | Miller . | |
| 915,913 | 3/1909 | Warren | 312/226 |
| 1,284,492 | 11/1918 | Thomas | 312/225 |
| 1,422,685 | 7/1922 | Fitchet | 350/615 |
| 1,671,231 | 5/1928 | Culbertson . | |
| 1,973,283 | 9/1934 | Buttrick | 350/615 |
| 2,145,462 | 1/1939 | Speck | 312/225 |
| 2,211,480 | 8/1940 | Ring | 88/1 |
| 2,763,186 | 9/1956 | Barlow | 350/615 |
| 2,908,465 | 10/1959 | Lykes | 248/166 |
| 3,336,606 | 9/1967 | Beitzel | 5/68 |
| 3,562,824 | 2/1971 | White | 5/61 |
| 3,868,103 | 2/1975 | Pageot et al. | 269/325 |
| 4,138,083 | 2/1979 | Spiegel | 248/474 |
| 4,188,740 | 2/1980 | Forman | 40/152 |
| 4,278,223 | 7/1981 | Fauteux | 248/125 |
| 4,686,355 | 8/1987 | Lay | 219/385 |

FOREIGN PATENT DOCUMENTS

| | | | |
|---|---|---|---|
| 516019 | 8/1955 | Canada | 350/615 |

*Primary Examiner*—Alvin C. Chin-Shue
*Assistant Examiner*—Robert A. Olson
*Attorney, Agent, or Firm*—Davis, Bujold & Streck

[57] ABSTRACT

An apparatus to permit anatomical self examination consisting of a support frame and at least one support arm secured to and extending from the support frame at an angle in an approximate range of between 85 and 150 degrees. A primary mirror is mounted to the support frame for pivotal movement about an horizontal axis. At least one secondary mirror is mounted to the support arm for omni-directional movement. By focusing one of the mirrors at the other of the mirrors an anatomical self examination may be performed.

5 Claims, 3 Drawing Sheets

10
16
22
42
34
26
48
36
38
30
12
44
18
40
50
36
32
52
28
24
34
38
14
20
42

10
12
14
16
18
20
22
24
26
28
38
38
40
42
42
44

APPARATUS TO PERMIT ANATOMICAL SELF EXAMINATION

The present invention relates to an apparatus to permit anatomical self examination.

BACKGROUND OF THE INVENTION

The human anatomy is such that, even for a healthy person, a thorough self examination of certain parts of the body is not possible. By way of illustration, it is difficult for a person to examine his or her own back and buttocks region. As a person gets older he or she becomes less flexible and the problem increases. Similarly, when a person is overweight his or her own bulk may prevent an examination of pelvic and other lower body regions.

The within invention was developed to meet the needs of a colostomy patient who required a visual anatomical examination of the affected area, while leaving the hands free to change the medical dressing.

SUMMARY OF THE INVENTION

What is required is an apparatus to permit anatomical self examination; and more particularly one which leaves the hands of the user free to change dressings or otherwise treat an affected area.

According to the present invention there is provided an apparatus to permit anatomical self examination comprised of a support frame and at least one support arm secured to and extending from the support frame at an angle in an approximate range of between 85 and 150 degrees. A primary mirror is mounted to the support frame for pivotal movement about an horizontal axis. At least one secondary mirror is mounted to the support arm for omni-directional movement. By focusing one of the mirrors at the other of the mirrors an anatomical self examination may be performed.

Although beneficial results may be obtained by using the apparatus as described, most dressings must be applied while the person is in a recumbent position. Even more beneficial results may therefore be obtained if the support frame has legs, such that the legs may straddle an anatomical frame of a person in a recumbent position.

Although beneficial results may be obtained by using the apparatus as described, the apparatus must be capable of being stored when not in use. Even more beneficial results may therefore be obtained if the support arm is pivotally mounted to the support frame such that the support arm may be moved between an operative position at an angle to the support frame in an approximate range of between 85 and 150 degrees and a stored position parallel to the support frame.

Although beneficial results may be obtained from using the apparatus as described, a balanced support configurationn provides greater stability and even better visibility. Even more beneficial results may therefore be obtained if there is a support arm at either end of the support frame.

Although beneficial results may be obtained from using the apparatus as described, when a person is applying dressings all necessary supplies must be within easy reach. Even more beneficial results may therefore be obtained if there is at least one storage shelf in the support arm.

Although beneficial results may be obtained from using the apparatus as described, when applying dressings it is desirable to have a light which can illuminate the affected area and a blow dryer to blow warm air at the affected area. Even more beneficial results may therefore be obtained if, there is at least one mounting bracket secured to the support frame, whereby a light or air dryer may be mounted.

BRIEF DESCRIPTION OF THE DRAWINGS

These and other features of the invention will become more apparent from the following description in which reference is made to the appended drawings, wherein.

DETAILED DESCRIPTION OF THE PREFERRED EMBODIMENT

Figure 1:
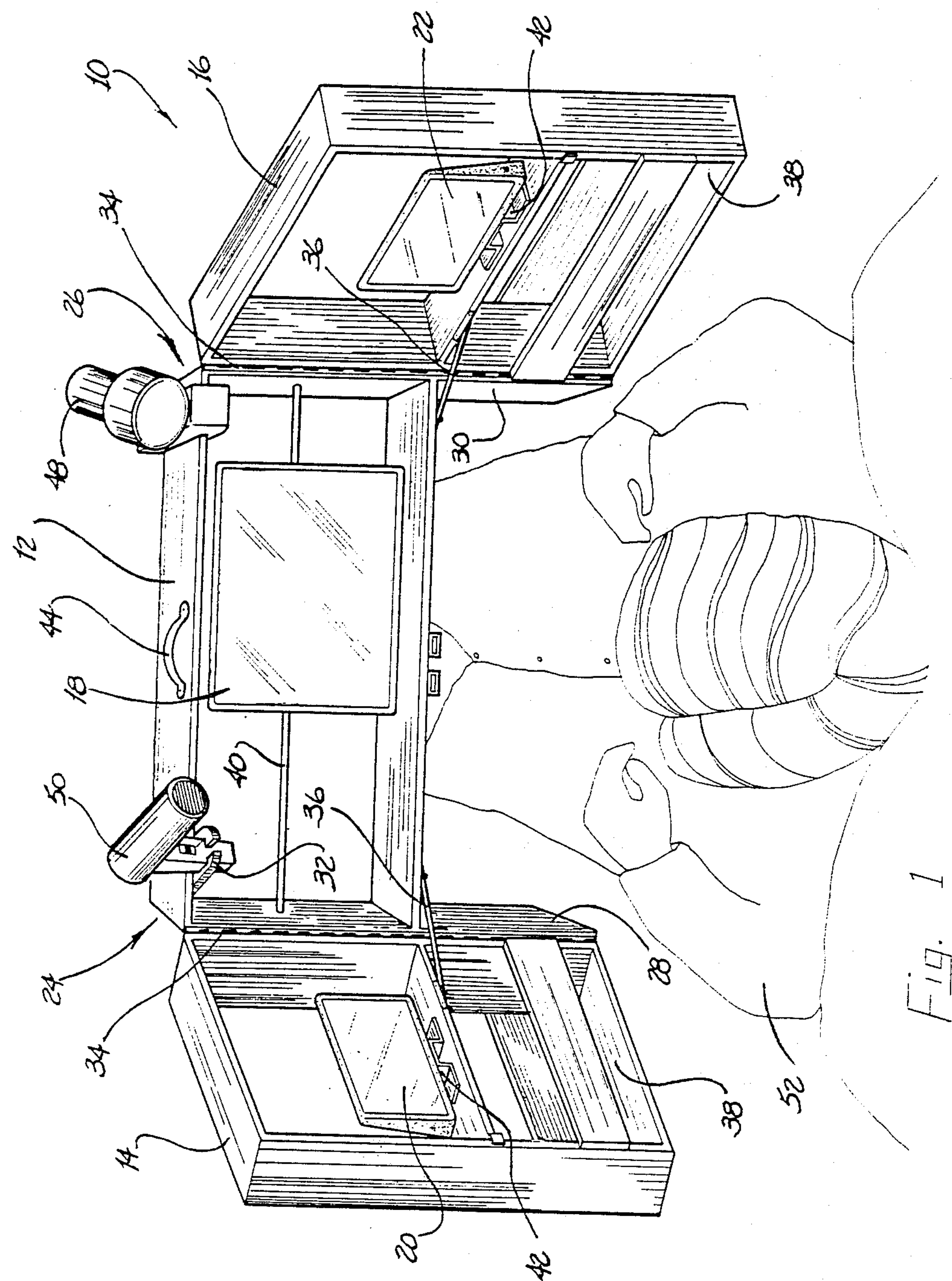
FIG. 1 is a perspective view of a preferred embodiment of the invention in an operative position.
Figure 2:
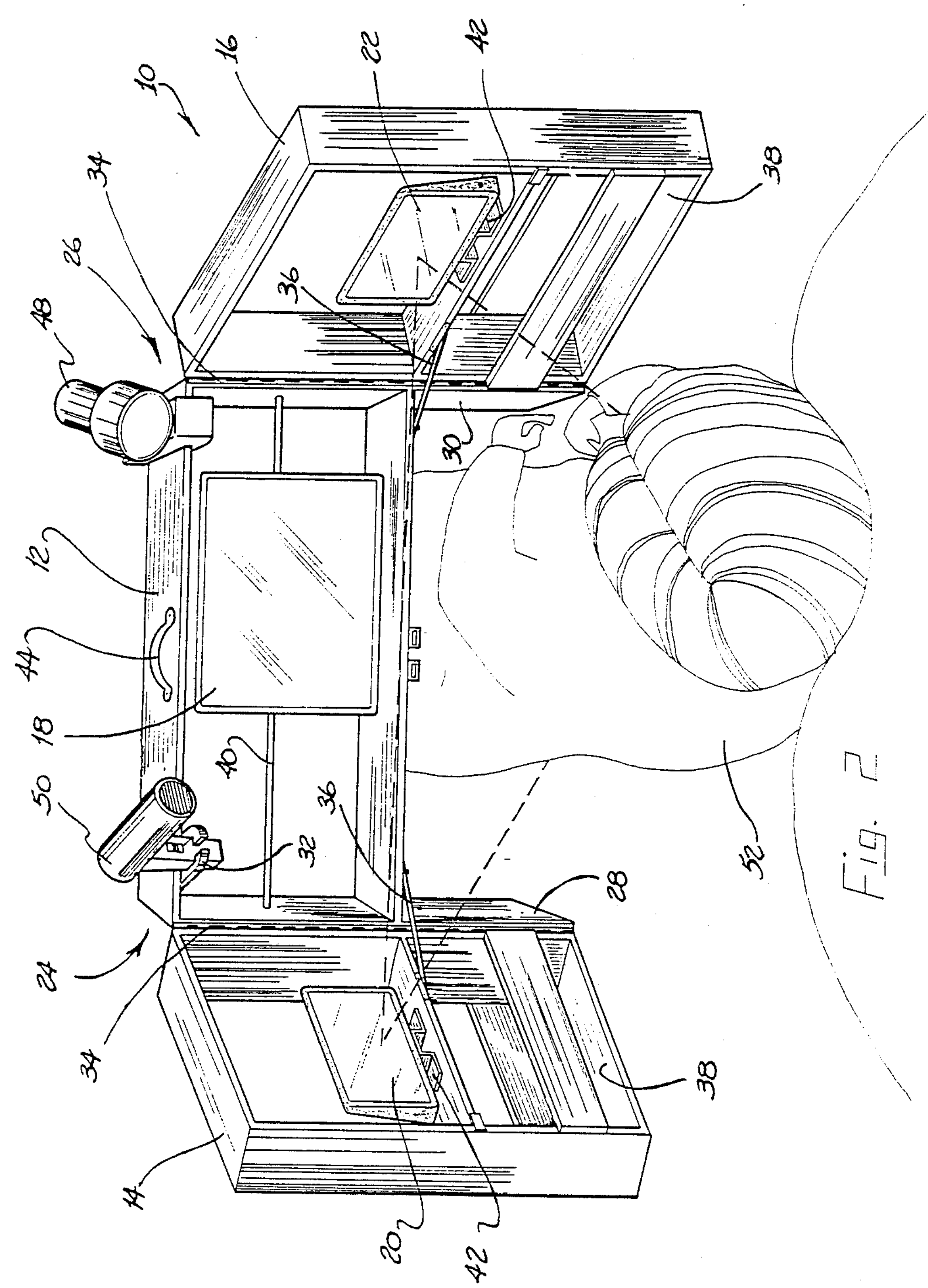
FIG. 2 is a perspective view of the apparatus illustrated in FIG. 1, being used by a patient for self examination.
Figure 3:
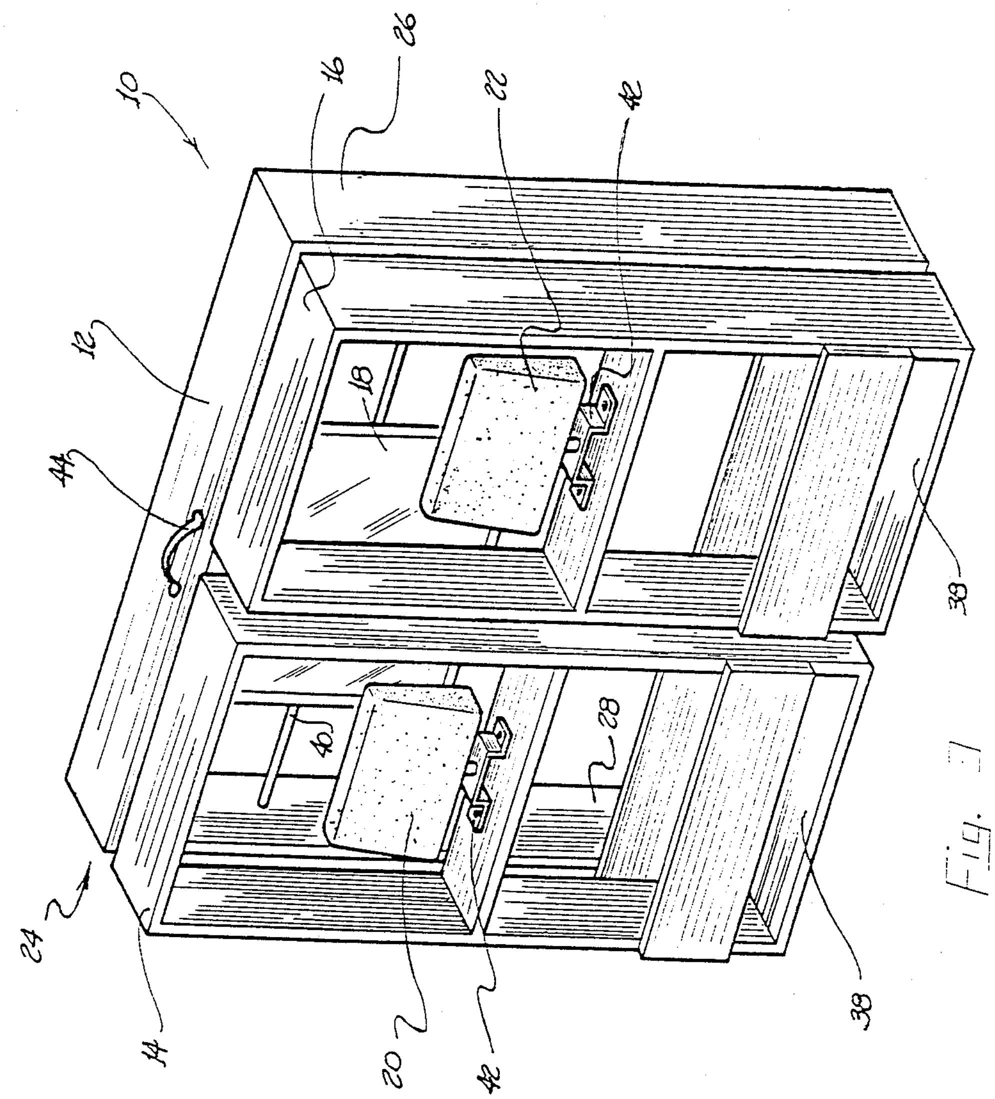
FIG. 3 is a perspective view the apparatus illustrated in FIG. 1 in a stored position.

The preferred embodiment will now be described with reference to FIGS. 1 through 3. The preferred embodiment, generally designated by reference numeral 10, is an apparatus to permit anatomical self examination. The primary components of apparatus 10 are a support frame 12, two support arms 14 and 16, a primary mirror 18, and two secondary mirrors 20 and 22.

Support frame 12 has opposed ends 24 and 26. Support frame 12 has a leg 28 which extends down from end 24, and a leg 30 which extends down from end 26. Support frame 12 has a mounting bracket 32. Support arm 14 is secured to and extends from end 24 of support frame 12. Support arm 16 is secured to and extends from end 26 of support frame 12. Both of support arms 14 and 16 are pivotally mounted to support frame 12 by piano hinges 34. Piano hinges 34 permit support arms 14 and 16 to be moved between an operative position at an angle in an approximate range of between 85 and 150 degrees in relation to support frame 12 and a stored position parallel to support frame 12. The operative position is illustrated in FIGS. 1 and 2. The stored position is illustrated in FIG. 3. In the preferred embodiment support arms 14 and 16 extend for the cumulative height of support frame 12 and legs 28 or 30, the purpose for this will be explained in relation to the description of the operation of the invention. A guide track 36 extends between support frame 12 and each of support arms 14 and 16. Each of support arms 14 and 16 has a storage shelf 38. Primary mirror 18 is pivotally mounted to a dowel 40 which extends horizontally between ends 24 and 26 of support frame 12. Dowel 40 provides a horizontal axis for the pivotal movement of primary mirror 18. Secondary mirror 20 is mounted to support arm 14, and secondary mirror 22 is mounted to support arm 16. Secondary mirrors 20 and 22 are mounted on a ball joint connection 42 which permits omni-directional adjustment. A handle 44 is positioned on support frame 12.

The use of apparatus 10 will now be explained with regard to FIGS. 1 through 3. Apparatus 10 starts in a stored position as illustrated in FIG. 3. In the stored position apparatus 10 may be transported by grasping handle 44. Apparatus 10 is then placed in an operative position as illustrated in FIG. 1. Support arms 14 and 16 extend the cumulative length of support frame 12 and legs 28 or 30, creating a triangular effect which gives apparatus 10 stability so the user need not worry about apparatus 10 falling down. Support arms 14 and 16 are positioned at an angle to support frame 12 to create the desired triangular effect. Guide track 36 prevents the selected positioning from being inadvertently altered during use. A light, which for the purpose of this description has been identified by reference numeral 48 is then mounted to support frame 12. A blow dryer, which for the purpose of this description has been identified by reference numeral 50, is positioned in mounting bracket 32. Referring to FIGS. 1 and 2, apparatus 10 is then placed in a position where legs 28 and 30 of support frame 12 straddle an anatomical frame of a person; the person being identified for the purpose of this description by reference numeral 52. A person 52 wishing to examine a portion of his anatomy may do so by assuming either a prone or a recumbent position. The person 52 may be able to view the desired portion of his anatomy by looking at only one of mirrors 18, 20 or 22. In some situations he may wish to look at each of mirrors 18, 20 and 22 in turn to obtain a three dimensional view of the affected area. By positioning of secondary mirror 20 adjusted to focus at primary mirror 18 the person 52 is able to view areas of his anatomy not visible by using a single mirror. Primary mirror 18 is then adjusted to focus at the desired portion of the anatomy not otherwise visible. By adjusting the positioning of primary mirror 18 and secondary mirror 20 person 52 is able to perform an anatomical self examination. The viewing area is further expanded if the person 52 assumes a fetal position. For example, if the person 52 assumes a fetal position from a recumbent position by drawing up his legs an examination of the anal area may be performed. The applicant recommends a preferred range of 85 to 150 degrees for the positioning of support arms 14 and 16 with respect to support frame 12. If support arm 14 is positioned at less than 85 degrees support arm 14 will start to obstruct the vision of a person 52 of primary mirror 18. Similarly, if support arm 14 is positioned at greater than 150 degrees the view of primary mirror 18 to a person 52 looking into secondary mirror 20 is not satisfactory. In FIG. 1, the person 52 is in a recumbent position, which would be assumed by a person changing a dressing on a colostomy or urostomy. It is of vital importance to such patients that they be able to change their own dressings; for if they are unable to do so they require institutional care. The person 52 in FIG. 1, tries to remain still and looks alternatively from mirror 18 to mirrors 20 and 22 to provide a three dimensional view. The three dimensional view is critical to a colostomy or urostomy patient as the dressing must be properly adhered around the entire circumference of the wound. The excrement produced by the human body can cause skin irritation, and the person must be in a position to view and treat the skin surrounding the affected area. Light 48 may be focused on the affected area to ensure visibility is not obscured by shadow. Blow dryer 50 may be used to warm and dry the affected area. Any necessary supplies may be stored within easy reach in shelves 38. Primary mirror 18 may be adjusted to focus on the affected area, and secondary mirror 20 may be adjusted to focus on primary mirror 18. In other applications the person 52 must use a combination of mirrors 18, and 22 in order to view the affected area, as is illustrated in FIG. 2. In experimental use by the applicants in a hospital setting, it has been found that bed sheets may be drawn over support frame 12 to provide the patient with privacy while changing dressings. Secondary mirrors 20 and 22 are expressed to be "omni-directional".

This is critical to the successful application of the invention. The Applicant attempted to construct a prototype in which secondary mirrors 20 and 22 pivoted on a fixed axis, however, this was not operable. In order to obtain the scope of vision required in this application, the movement must be omni-directional. For clarification, by the use of the term "omni-directional" the applicant means that both the horizontal and vertical planes of mirrors 20 and 22 must be capable of adjustment.

It will be apparent to one skilled in the art that the present invention permits anatomical self examination; and more particularly leaves the hands of the user free to change dressings or otherwise treat an affected area during the course of such examination. It will also be apparent to one skilled in the art that modifications may be made to the preferred embodiment without departing from the spirit and scope of the invention. In particular, apparatus 10 could be made operable with only one of support arms 14 or 16. Support arms 14 or 16 needs not extend the cumulative height of support frame 12 and legs 28 and 30 if other means were employed to provide apparatus 10 with stability. Apparatus 10 would be operable without mounting bracket 32, or shelves 38. Apparatus 10 would be operable even if support arms 14 and 16 were not capable of being placed into a stored position. Apparatus 10 would be operable in a form other than one which straddles the anatomical frame of the patient.

The embodiments of the invention in which an exclusive property or privilege is claimed are defined as follows:

1. An apparatus to permit anatomical self examination, comprising:

a. a support frame having opposed ends, the support frame having legs, whereby the support frame may straddle an anatomical frame of a person in a recumbent position;

b. a support arm secured to and extending from each of the ends of the support frame at an angle in an approximate range of between 85 and 150 degrees, the support arm being pivotally mounted to the support frame such that the support arm may be moved between an operative position at an angle in an approximate range to the support frame of between 85 and 150 degrees and a stored position parallel to the support frame;

c. a primary mirror mounted to the support frame for pivotal movement about an horizontal axis; and d. a secondary mirror mounted to each of the support arms for omni-directional movement, such that by focusing one of the mirrors at another of the mirrors an anatomical self examination may be performed.

2. An apparatus to permit anatomical self examination as defined in claim 1, having means to secure the support arm in an operative position.

3. An apparatus to permit anatomical self examination as defined in claim 1, having at least one mounting bracket secured to the support frame, whereby a light or air dryer may be mounted.

4. An apparatus to permit anatomical self examination as defined in claim 1, having at least one storage shelf in the support arm.

5. An apparatus to permit anatomical self examination, comprising:

a. a support frame having opposed ends, the support frame having legs of an appropriate length whereby the support frame may straddle an anatomical frame of a person in a recumbent position;

b. a support arm secured to and extending from each of the ends of the support frame at an angle in an approximate range of between 85 and 150 degrees, the support arm being pivotally mounted to the support frame such that the support arm may be moved between an operative position, at an angle in an approximate range to the support frame of between 85 and 150 degrees, and a stored position parallel to the support frame;

c. a primary mirror mounted to the support frame for pivotal movement about a horizontal axis; and d. a secondary mirror mounted to each of the support arms for omni-directional movement, such that by focusing one of the mirrors at another of the mirrors an anatomical self examination may be performed;

wherein the legs are of a length sufficient only to support the apparatus immediately above the person in a recumbent position whereby the mirrors of the apparatus may be positioned to allow that recumbent person to view desired parts of that person's anatomy without obstruction from the apparatus.

* * * * *